United States Patent [19]
Markos

[11] 3,974,143
[45] Aug. 10, 1976

[54] (16α)-16,17-ALKYLIDENEBIS(OXY)-3-ARYLPREGNA-2,4,6-TRIEN-20-ONES

[75] Inventor: Charles S. Markos, Skokie, Ill.

[73] Assignee: G. D. Searle & Co., Chicago, Ill.

[22] Filed: Sept. 19, 1975

[21] Appl. No.: 614,938

[52] U.S. Cl. .................... 260/239.55 D; 424/241
[51] Int. Cl.² ................................. C07J 21/00
[58] Field of Search ................. 260/239.55 D Primary Examiner—Elbert L. Roberts
Attorney, Agent, or Firm—John M. Brown

[57] ABSTRACT

Preparation of (16α)-16,17-alkylidenebis(oxy)-3-arylpregna-2,4,6-trien-20-ones and their progestational and glucocorticoid antiinflammatory utility are disclosed.

12 Claims, No Drawings

(16α)-16,17-ALKYLIDENEBIS(OXY)-3-ARYL-PREGNA-2,4,6-TRIEN-20-ONES

This invention relates to (16α)-16,17-alkylidenebis-(oxy)-3-arylpregna-2,4,6-trien-20-ones and processes for the preparation thereof. More particularly, this invention provides new, useful, and unobvious chemical compounds of the formula

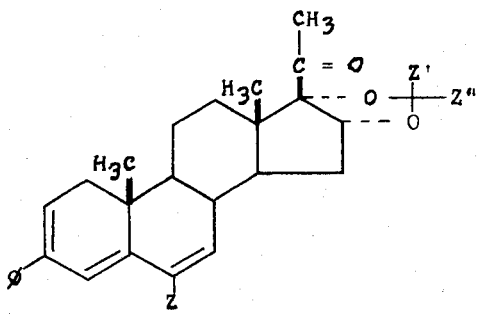

wherein φ represents phenyl optionally substituted by alkyl, halogen, and/or alkoxy; Z represents hydrogen, alkyl, or halogen; Z' represents hydrogen or alkyl; and Z" represents alkyl.

Among the alkyls contemplated by φ (as phenyl substituents), Z, Z', and Z", lower alkyls are preferred, which is to say methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, and like monovalent, saturated, acyclic straight- or branched-chain hydrocarbon groupings of the formula

$C_nH_{2n+1}$ wherein n represents a positive integer less than 8.

The halogens contemplated by φ (as substituents) are fluorine, chlorine, and bromine; those contemplated by Z are fluorine and chlorine.

The alkoxys contemplated by φ (as substituents), like the alkyls aforesaid, are preferably of lower order, and accordingly have the formula

$-OC_nH_{2n+1}$ wherein n is as previously defined.

A plurality of substituents, alike or different can be present in the phenyl nucleus comprehended by φ albeit a single substituent — if any — is preferred. Positioning of the substituent(s) relative to the point of attachment of the phenyl nucleus to the steroid skeleton or, where more than 1 substituent is present, to each other is not critical, excepting that halogen ortho to the point of attachment of the phenyl nucleus to the steroid skeleton is excluded.

The compounds to which this invention relates are useful by reason of their valuable biological properties. Thus, for example, they are progestational and — more important — glucocorticoid antiinflammatory agents.

The progestational utility of the instant compounds can be demonstrated by the standardized test described in U.S. Pat. No. 3,539,538. So tested (16α)-6-methyl-16,17-[(1-methylethylidene)bis(oxy)]-3-phenylpregna-2,4,6-trien-20-one, the product of Example 2 hereinafter, was found to be about 5% as potent as progesterone when administered buccally.

The antiinflammatory utility of the instant compounds can be demonstrated by a standardized test for their capacity to inhibit the edema induced in rats by injection of *Mycobacterium butyricum*. The procedure, which is similar to one described by Pearson et al. in Arthritis Rheumat., 2, 440 (1959), follows. Intact male Sprague-Dawley rats (60–70 grams) are randomized in groups pf 12, one group for each compound to be tested plus one group to serve as controls. Each animal is injected intradermally (without any anesthesia) on the base of the tail with 2.0 mg. of dry, heat-killed *Mycobacterium butyricum* (Difco 0640–33) suspended in 0.05 ml. of paraffin oil, whereupon the prescribed dose of compound, dissolved or suspended in a vehicle consisting of 0.5 ml. of either corn oil or a mixture of 20 ml. of aqueous 0.85% sodium chloride with 1 drop of polysorbate 80, is intragastrically or subcutaneously administered. Administration thus of compound is repeated daily for the next 18 consecutive days, the initial dose ordinarily being 10 mg/kg/day intragastrically. The control group is identically and concurrently administered vehicle alone. On the 20th day, the rats are sacrificed and the total volume of each pair of hind feet is measured in arbitrary units. A compound is considered antiinflammatory if the average volume (T) of the hind feet in the group treated therewith is significantly ($P \leq 0.05$) less than the corresponding value (C) for the control group. Hydrocortisone administered intragastrically has an $Ed_{50}$ of approximately 7.0 mg/kg/day in this test. The $ED_{50}$ of (16α)-6-methyl-16,17-[(1-methylethylidene)bis(oxy)]-3-phenylpregna-2,4,6-trien-20-one in said test was found to be 1.2 mg/kg/day.

The biological activity of (16α)-6-methyl-16,17-[(1-methylethylidene)bis(oxy)]-3-phenylpregna-2,4,6-trien-20-one in the tests referred to above is specified merely for purposes of illustration, and is accordingly not to be construed as either delimiting or exclusionary.

Those skilled in the art will recognize that observations of activity in standardized tests for particular biological effects are fundamental to the development of valuable new drugs, both veterinary and human.

Preparation of the compounds of this invention proceeds by contacting a tetrahydrofuran solution of a steroid of the formula

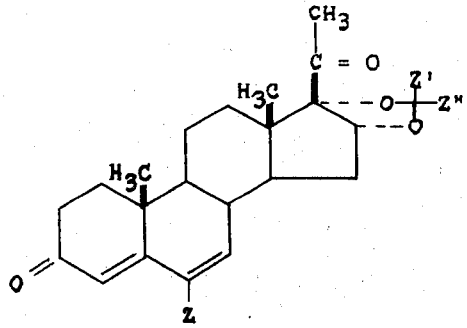

with an ether solution of a Grignard reagent of the formula

φ Mg Br and acidifying the resultant mixture with hydrochloric acid. The steroidal starting materials are well-known in the art [J. Amer. Chem. Soc., 82, 2840 (1960); U.S. Pat. No. 3,257,587 and 3,445,462; Brit. 1,042,193; etc.], as are the Grignard reagents called for.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A solution of 27 parts of bromophenylmagnesium in 40 parts of 1,1'-oxybisethane is added, with stirring, to a cooled solution of 12 parts of (16α)-16,17-[(1-methylethylidene)bis(oxy)[pregna-4,6-diene-3,20-dione [J. Amer. Chem. Soc., 82, 2840 (1960)]in 200 parts of tetrahydrofuran at a rate such that temperatures in the range, 15°–20° are maintained. Approximately 20 minutes after completion of the addition, 50 parts of methanol, followed by 40 parts of 20% hydrochloric acid are introduced. The resultant mixture is stripped of organic solvents by vacuum distillation. To the aqueous residue is added just sufficient methanol to effect solution at the boiling point. The solution is chilled, whereupon the precipitate which forms is isolated by filtration, washed with water, and dried in air. The product thus isolated is (16α)-16,17-[(1-methylethylidene)bis(oxy)]-3-phenylpregna-2,4,6-trien-20-one, having the formula

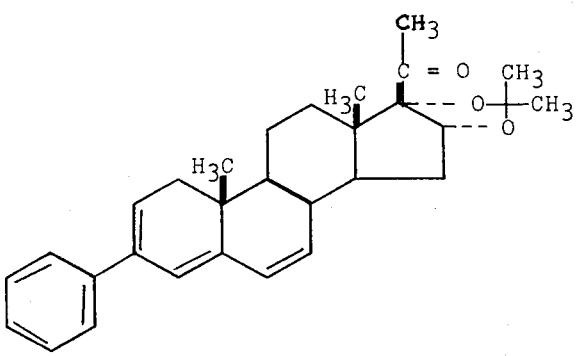

EXAMPLE 2

A solution of 27 parts of bromophenylmagnesium in 40 parts of 1,1'-oxybisethane is added, with stirring, to a cooled solution of 12 parts of (16α)-6-methyl-16,17-[(1-methylethylidene)bis(oxy)]pregna-4,6-diene-3,20-dione (U.S. Pat. No. 3,157,387) in 200 parts of tetrahydrofuran at a rate such that temperatures in the range, 15°–20° are maintained. Approximately 20 minutes after completion of the addition, 50 parts of methanol, followed by 40 parts of 20% hydrochloric acid are introduced. The resultant mixture is stripped of organic solvents by vacuum distillation. To the aqueous residue is added 200 parts of methanol. The mixture thus obtained is heated to boiling and then chilled, whereupon the precipitate which forms is isolated by filtration, washed with water, and dried in air. The product thus isolated is (16α)-6-methyl-16,17-[(1-methylethylidene)-bis(oxy)]-3-phenylpregna-2,4,6-trien-20-one, which, recrystallized from a mixture of methanol and dichloromethane, melts at 169°–171°. The product has the formula

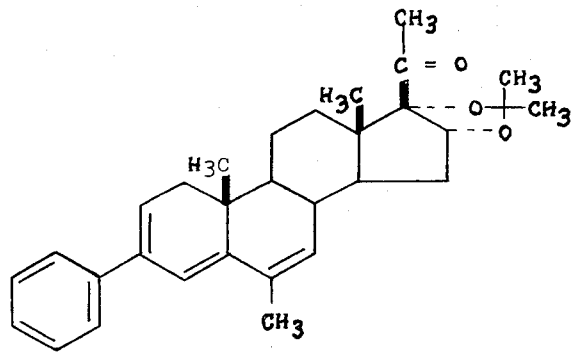

EXAMPLE 3

Substitution of 27 parts of bromo-(o-methylphenyl)-magnesium for the bromophenylmagnesium called for in Example 2 affords, by the procedure there detailed, (16α)-6-methyl-16,17-[(1-methylethylidene)bis(oxy)]-3-o-methylphenyl)pregna-2,4,6-trien-20-one melting at 164°–166°. The product has the formula

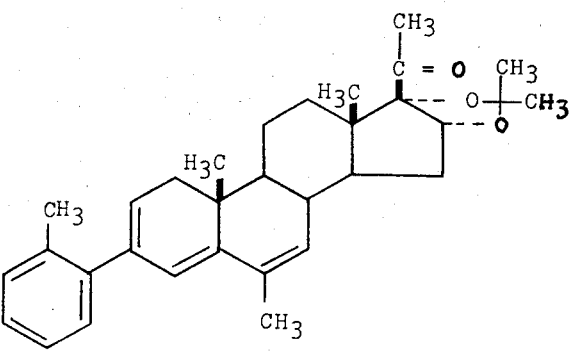

EXAMPLE 4

Substitution of 27 parts of bromo-(p-methylphenyl)-magnesium for the bromophenylmagnesium called for in Example 2 affords, by the procedure there detailed, (16α)-6-methyl-16,17-[(1-methylethylidene)bis(oxy)]-3-(p-methylphenyl)pregna-2,4,6-trien-20-one melting at 165°–170°.

EXAMPLE 5

A solution of 27 parts of bromo-(p-ethylphenyl)magnesium in 40 parts of 1,1'-oxybisethane is added, with stirring, to a cooled solution of 12 parts of (16α)-6-methyl-16,17-[(1-methylethylidene)bis(oxy)]pregna-4,6-diene-3,20-dione in 200 parts of tetrahydrofuran at a rate such that temperatures in the range, 15°–20° are maintained. Approximately 20 minutes after completion of the addition, 50 parts of methanol, followed by 40 parts of 20% hydrochloric acid are introduced. The resultant mixture is stripped of organic solvents by vacuum distillation. To the aqueous residue is added just sufficient methanol to effect solution at the boiling point. The solution is chilled, whereupon the precipitate which forms is isolated by filtration, washed with water, and dried in air. The product thus isolated is (16α)-3-(p-ethylphenyl)-6-methyl-16,17-[(1-methylethylidene)bis(oxy)]pregna-2,4,6-trien-20-one.

EXAMPLE 6

Substitution of 27 parts of bromo-(m-fluorophenyl-magnesium for the bromophenylmagnesium called for in Example 2 affords, by the procedure there detailed, (16α)-3-(m-fluorophenyl)-6-methyl-16,17-[(1-methylethylidene)bis(oxy)]-pregna-2,4,6-trien-20-one melting at 165°–170°.

EXAMPLE 7

Substitution of 27 parts of bromo-(p-fluorophenyl)-magnesium for the bromophenylmagnesium called for in Example 2 affords, by the procedure there detailed, (16α)-3-(p-fluorophenyl)-6-methyl-16,17-[(1-methylethylidene)bis(oxy)]-pregna-2,4,6-trien-20-one melting at 154°–157°.

EXAMPLE 8

Substitution of 27 parts of bromo-(m-bromophenyl)-magnesium for the bromo-(p-ethylphenyl)magnesium called for in Example 5 affords, by the procedure there detailed, (16α)-3-(m-bromophenyl)- 6-methyl-16,17-[(1-methylethylidene)-bis(oxy)]pregna-2,4,6-trien-20-one.

EXAMPLE 9

Substitution of 27 parts of bromo-(p-methoxyphenyl)magnesium for the bromophenylmagnesium called for in Example 2 affords, by the procedure there detailed, (16α)-3-(p-methoxyphenyl)-6-methyl-16,17-[(1-methylethylidene)bis(oxy)]pregna-2,4,6-trien-20-one melting at 150°–154°.

EXAMPLE 10

Substitution of 27 parts of bromo-(p-ethoxyphenyl)-magnesium for the bromo-(p-ethylphenyl)magnesium called for in Example 5 affords, by the procedure there detailed, (16α)-3-(p-ethoxyphenyl)-6-methyl-16,17-[(1-methylethylidene)bis(oxy)]pregna-2,4,6-trien-20-one.

EXAMPLE 11

Substitution of 12 parts of (16α)-16,17-[ethylidenebis(oxy)]-6-methylpregna-4,6-diene-3,20-dione (U.S. Pat. No. 3,257,387) for the (16α)-16,17-[(1-methylethylidene)bis-(oxy)]pregna-4,6-diene-3,20-dione called for in Example 1 affords, by the procedure there detailed, (16α)-16,17-[ethylidenebis(oxy)]-6-methyl-3-phenylpregna-2,4,6-trien-20-one.

EXAMPLE 12

Substitution of 12 parts of (16α)-6-methyl-16,17-[(1-methylpropylidene)bis(oxy)]pregna-4,6-diene-3,20-dione (U.S. Pat. No. 3,257,387) for the (16α)-16,17-[(1-methylethylidene)-bis(oxy)]pregna-4,6-diene-3,20-dione called for in Example 1 affords, by the procedure there detailed, (16α)-6-methyl-16,17-[(1-methylpropylidene)bis(oxy)]-3-phenylpregna-2,4,6-trien-20-one.

EXAMPLE 13

Substitution of 12 parts of (16α)-16,17-[(1-ethylpropylidene)bis(oxy)]-6-methylpregna-4,6-diene-3,20-dione (U.S. Pat. No. 3,257,387) for the (16α)-16,17-[(1-methylethylidene)bis(oxy)]pregna-4,6-diene-3,20-dione called for in Example 1 affords, by the procedure there detailed, (16α)-16,17-[(1-ethylpropylidene)bis(oxy)]-6-methyl-3phenylpregna-2,4,6-trien-20-one.

EXAMPLE 14

Substitution of 12 parts of (16α)-6-fluoro-16,17-[(1-methylethylidene)bis(oxy)]pregna-4,6-diene-3,20-dione (U.S. Pat. No. 3,445,462) for the (16α)-16,17-[(1-methylethylidene)bis(oxy)]pregna-4,6-diene-3,20-dione called for in Example 1 affords, by the procedure there detailed, (16α)-6-fluoro-16,17-[(1-methylethylidene)bis-(oxy)]-3-phenylpregna-2,4,6-trien-20-one.

EXAMPLE 15

Substitution of 12 parts of (16α)-6-chloro-16,17-[(1-methylethylidene)bis(oxy)]pregna-4,6-diene-3,20-dione (U.S. Pat. No. 3,445,462) for the (16α)-16,17-[(1-methylethylidene)bis(oxy)]pregna-4,6-diene-3,20-dione called for in Example 1 affords, by the procedure there detailed, (16α)-6-chloro-16,17-[(1-methylethylidene)bis(oxy)]-3-phenylpregna-2,4,6-trien-20-one.

What is claimed is:

1. A compound of the formula

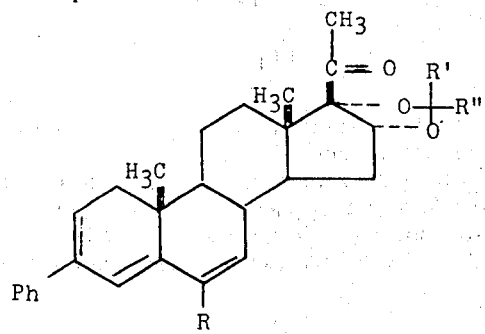

wherein Ph represents phenyl, alkylphenyl in which the alkyl contains fewer than 8 carbons, alkoxyphenyl in which the alkoxy contains fewer than 8 carbons, or halophenyl in which the halogen is meta or para fluorine, chlorine, or bromine; R represents hydrogen, methyl, fluorine, or chlorine; R' represents hydrogen or alkyl containing fewer than 8 carbons; and R'' represents alkyl containing fewer than 8 carbons.

2. A compound according to claim 1 having the formula

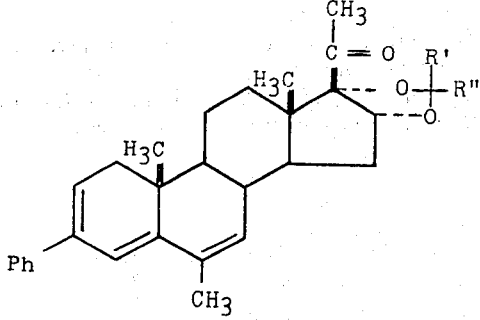

wherein Ph represents phenyl optionally substituted by alkyl containing fewer than 8 carbons and R' and R'' each represent alkyl containing fewer than 8 carbons.

3. A compound according to claim 1 having the formula

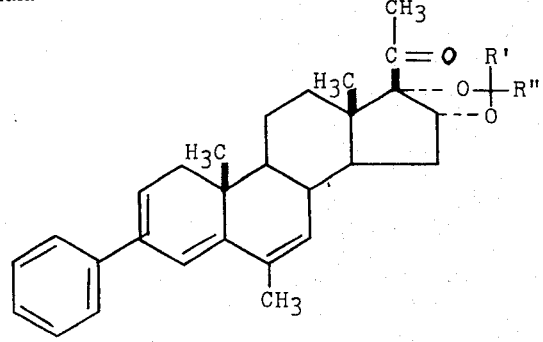

wherein R' and R'' each represent alkyl containing fewer than 8 carbons.

4. A compound according to claim 1 which is (16α)-6-methyl-16,17-[(1-methylethylidene)bis(oxy)]-3-phenylpregna-2,4,6-trien-20-one.

5. A compound according to claim 1 having the formula

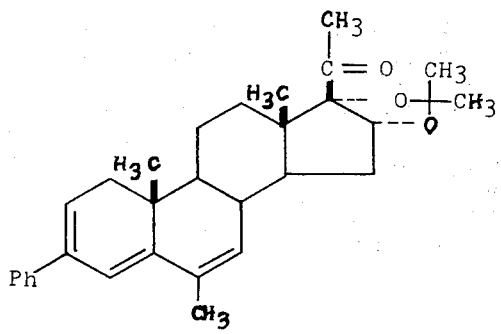

wherein Ph represents alkylphenyl in which the alkyl contains fewer than 8 carbons.

6. A compound according to claim 1 which is (16α)-6-methyl-3-(o-methylphenyl)-16,17-[(1-methylethylidene)bis(oxy)]phenylpregna-2,4,6-trien-20-one.

7. A compound according to claim 1 having the formula

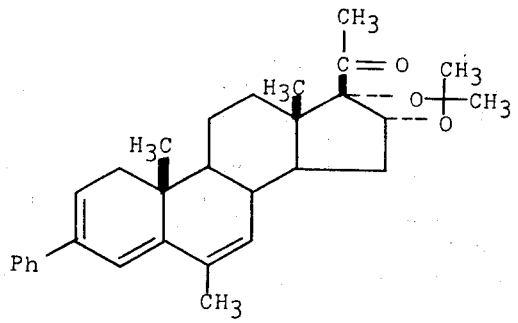

wherein Ph represents halophenyl in which the halogen is meta or para fluorine, chlorine, or bromine.

8. A compound according to claim 1 which is (16α)-3-(p-fluorophenyl)-6-methyl-16,17-[(1-methylethylidene)bis(oxy)]phenylpregna-2,4,6-trien-20-one.

9. A compound according to claim 1 having the formula

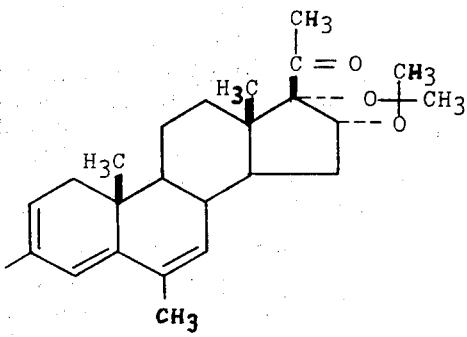

wherein Ph represents alkoxyphenyl in which the alkoxy contains fewer than 8 carbons.

10. A compound according to claim 1 which is (16α)-3-(p-methoxyphenyl)-6-methyl-16,17-[(1-methylethylidene)bis(oxy)]phenylpregna-2,4,6-trien-20-one.

11. A compound according to claim 1 having the formula

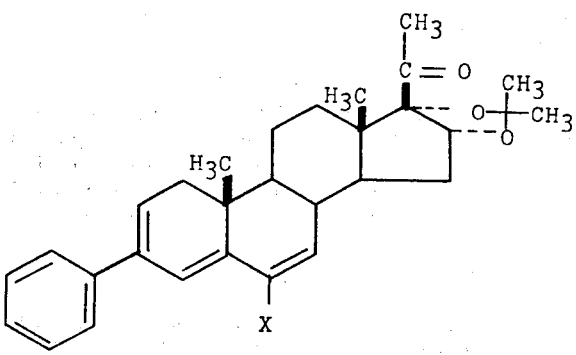

wherein X represents fluorine or chlorine.

12. A compound according to claim 1 which is (16α)-6-chloro-16,17-[(1-methylethylidene)bis(oxy)]-3-phenylpregna-2,4,6-trien-20-one.

* * * * *